United States Patent [19]

Kiedik et al.

[11] Patent Number: 5,470,809
[45] Date of Patent: Nov. 28, 1995

[54] METHOD TO TREAT AN ION-EXCHANGER CATALYST FOR THE PROCESS TO SYNTHESIZE ALKYLPHENOLS

[75] Inventors: Maciej Kiedik; Andrzej Krueger, both of Kędzierzyn-Koźle; Józef Kołt, Zabrze; Bogusław Tkacz, Kędzierzyn-Koźle; Tatiana Pers, Kędzierzyn-Koźle; Teresa Rdesinska-Cwik, Kędzierzyn-Koźle; Jan Niedziela, Kobylice; Ryszard Kosciuk, Kędzierzyn-Koźle; Anna Rzodeczko, Kędzierzyn-Koźle; Zbigniew Swiderski, Kędzierzyn-Koźle; Władysład Jankowski, Kędzierzyn-Koźle, all of Poland

[73] Assignees: Instytut Ciezniej Syntezy Organicznej Blachownia; Zaklady Chemiczne Blachownia, both of Kedzierzyn-Kozle, Poland

[21] Appl. No.: 240,239

[22] Filed: May 10, 1994

[30] Foreign Application Priority Data

May 14, 1993 [PL] Poland .................... P-298970

[51] Int. Cl.$^6$ .................................................. B01J 37/30
[52] U.S. Cl. ................... 502/12; 502/159; 568/716
[58] Field of Search ................ 502/12, 159; 521/32, 521/33; 568/716

[56] References Cited

U.S. PATENT DOCUMENTS 4,820,740  4/1989  Li ............................................. 521/32

Primary Examiner—Michael Lusignan
Attorney, Agent, or Firm—Bauer & Schaffer

[57] ABSTRACT

An ion-exchanger catalyst in the form of an acid ion-exchanger resin used for the synthesis process of alkylated phenols and having substitutes containing 6–12 carbon atoms in a chain is treated with phenol alkylation having olefins in the presence of acid catalysts such as acid ion-exchange resins.

1 Claim, No Drawings

METHOD TO TREAT AN ION-EXCHANGER CATALYST FOR THE PROCESS TO SYNTHESIZE ALKYLPHENOLS

This invention is directed to a method for the preparation of an ion-exchanger catalyst in the form of an acid ion-exchanger resin for use in the synthesis of alkylated phenols having substitute chains containing 6–12 carbon atoms. Phenol alkylation with olefins is effected in the present of acid catalysts such as acid ion-exchange resins. Commercial cation exchangers are most commonly used in alkylphenols synthesis processes directly as provided by the manufacturer in dry form. It is a rare practice to further treat the cation exchanger prior to use in the process.

According to Patent GB 981 828, a cation exchanger in the form of a sulphonated styrene-divinylbenzene copolymer, containing 2–8% by weight of divinylbenzene, is dried by heating with phenol and a solvent form an azeotropic mixture with water, the mixture having a boiling point higher than that of water and lower than that of phenol, as for example toluene. Following separation from the cation exchanger, water is distilled as an azeotrope at a temperature not lower than 150° C. Treatment of the cation exchanger is continued to release and remove water in an amount of not less than 1–3 % of dry matter of the cation exchanger. The resulting cation exchanger is sufficiently crosslinked and gelation-proof in the presence of phenol. In the alkylation process, such cation exchanger shows higher activity, selectivity and longer life. The resultant product is lighter in coloration and has a higher para isomer content.

Similar properties are exhibited by macroporous cation exchangers, newly developed by manufacturers of ion-exchanger resins. They are characterized by higher crosslinking degrees so as to not necessitate such aforementioned treatment.

Macroporous cation exchangers are known to acidify the postreaction mixture to a greater extent than the gel-type species. Thus, it is necessary to use an anion exchanger in the synthesis of alkyl phenols, in the presence of these macroporous cation exchangers. The anion exchanger, however, will release free amines, the presence of which cause the alkylation product to deteriorate in quality.

Another problem encountered in the known processes of manufacturing alkyl phenols alkylphenols is the presence of sulphur in the final product, which has an adverse effect on its color stability.

The object of this invention is to develop a method for treatment of a cation exchanger to be used as a catalyst in the synthesis of alkyl phenols which will lead to a reduction of the sulphur content of alkyl phenol products obtained during the alkylation without constantly having to use an anion exchanger.

Unexpectedly, it has been found that the repeated treatment of the wet cation exchanger with phenol and a liquid mixture of a specified composition, at a certain temperature, where the phenol and liquid mixture are brought into contact with an anion exchanger after each treatment and recycled in the cation exchanger treatment process produces a catalyst which, when used in the alkylation process, results in a product with a positively lower sulphur content.

In accordance with the present invention, a bed consisting of a wet cation exchanger, in the form of a sulphonated styrene-divinylbenzene copolymer, is washed with phenol having a water content of 0.01–1% by weight, at a temperature in the range 50°– 100° C. The resultant washings, containing 50–99.5% by weight of phenol and 0.5–50% by weight of water, are brought into contact with a basic ion-exchange resin, and then are distilled to remove water and produce a dewatered phenol, containing 0.01–1% water by weight. This dewatered phenol is used to wash the wet cation exchanger again. The washing of the cation exchanger bed with the dewatered phenol is repeated until a water content of the cation exchanger is not more than 10% by weight.

The cation exchanger bed is then washed at 60°–130° C. with a mixture containing 35–80% by weight phenol, 5–20% by weight $C_6$–$C_{12}$ olefins, 5–60% by weight alkyl phenols with substitute chains containing 6–12 carbon atoms, 0.1–5% by weight of dialkyl phenols with substitute chains containing 6–12 carbon atoms, 0.1–15% by weight of dialkyl phenols with substitute chains containing 6–12 carbon atoms, 0.1–15% by weight saturated $C_6$–$C_{12}$ hydrocarbons, and 0.05–2% by weight water. The resultant washings are then brought into contact with a basic ion-exchange resin and used to wash the cation exchanger bed again. Such treatment is continued until the moisture content of the cation exchanger is reduced to not more than 3% by weight.

Following this treatment, the cation exchanger, when used in the alkyl phenol synthesis as a catalyst, permits the 10 times reduction of the sulfur content of alkyl phenol products. Furthermore, it permits the total elimination of free amines from the final product since the anion exchanger is used only in the treatment of the cation exchanger which will be used as a catalyst and not during the actual synthesis of the alkyl phenols.

EXAMPLES 1–7

As seen in Table 1 100 ml of the sulphonated cation exchanger in hydrogen form, having a predetermined moisture content is packed in a glass column (25 mm in diameter).

The glass column $K_1$ is equipped with a heating jacket and directly connected to a second glass column $K_2$ (15 mm in diameter) also having a heating jacket. The second column $K_2$ is packed with 30 ml of Amberlyst A-21, an anion exchanger in the form of a weakly basic ion-exchange resin having tertiary amine functional groups. Treatment of the cation exchanger is effected by directing, to the first column $K_1$, an appropriate liquid stream which, at a specific flowrate and controlled temperature, $T_{K1}$, flows downward, first through the cation exchanger bed (Column $K_1$), then through the anion exchanger bed (second Column $K_2$) at temperature $T_{K2}$. Phenol containing 0.3% by weight water is used initially for washing the cation exchanger bed; the washings being dewatered by distillation, prior to being recycled in the cation exchanger treatment process. A mixture containing phenol, $C_6$–$C_{12}$ olefins, alkyl phenols and dialkyl phenols with substitute chains containing 6–12 carbon atoms, $C_6$–$C_{12}$ paraffins, and a small amount of water is then circulated through the columns packed with the cation and anion exchanger beds (Examples 2–7). For comparison, a stream of phenol alone was used for treating the cation exchanger in Example 1. The moisture content of the cation exchanger was determined at intervals during the treatment.

The treated cation exchanger was used as a catalyst in the synthesis of alkyl phenols. A 250-ml glass flask equipped with a magnetic stirrer was filled with 30 ml of the treated cation exchanger and 200 g of a mixture of phenol and an applicable propylene oligomer, that is propylene dimer, trimer or tetramer. The reaction of phenol alkylation was conducted for 5 hrs after which the resulting alkylate was vacuum-distilled at 50 mm Hg to recover alkyl phenol of which the purity was not lower than 97% and of which the sulphur content was also determined as seen in Table 3.

Shown in Table 1 are the treated species of cation exchangers, the treatment process parameters and the content of moisture in the cation exchanger. Table 2 shows compositions of the streams employed for treating the cation exchangers and Table 3 shows the conditions of synthesis and recovery, and the sulphur content determined in the alkylphenols obtained.

TABLE 1

| Example number | Cation exchanger Name | DVB percentage | N° of stream used for treatment of cation exchanger with composition acc. to Table 2 | Rate of liquid flow through Columns $K_1$ and $K_2$ [dm³/hr] | Bed temperature in Columns [°C.] $T_{K1}$ | $T_{K2}$ | Moisture content in cation-exchanger before treatment | after treatment |
|---|---|---|---|---|---|---|---|---|
| 1 (comparative) | Amberlyst-19 | 8 | 1 | 0.1 | 70 | 70 | 61.2 | 2.8 |
| 2 | Amberlyst-19 | 8 | 1 | 0.3 | 80 | 75 | 61.2 | 9.4 |
|   |              |   | 3 | 0.3 | 100 | 90 | 9.4 | 2.7 |
| 3 | Amberlyst-19 | 8 | 1 | 0.1 | 45 | 41 | 61.2 | 8.6 |
|   |              |   | 4 | 0.1 | 110 | 100 | 8.6 | 1.9 |
| 4 | Wofatit FK-4 | 4 | 1 | 0.2 | 70 | 70 | 67.8 | 9.0 |
|   |              |   | 5 | 0.2 | 130 | 120 | 9.9 | 3.0 |
| 5 | Amberlyst-16 | 12 | 1 | 0.05 | 100 | 100 | 57.3 | 7.2 |
|   |              |   | 4 | 0.05 | 120 | 110 | 7.2 | 2.1 |
| 6 | Amberlyst-15 | 20 | 1 | 0.4 | 70 | 60 | 51.2 | 7.9 |
|   |              |   | 6 | 0.4 | 90 | 80 | 7.9 | 1.4 |
| 7 | AmberlystXN 1010 | 50 | 1 | 0.2 | 60 | 50 | 24.3 | 8.1 |
|   |              |   | 2 | 0.2 | 60 | 50 | 8.1 | 2.2 |

TABLE 2

| Cation-exchanger stream number acc. to Table 1 | Stream composition [1% by weight] | | | | | | | | | | | |
|---|---|---|---|---|---|---|---|---|---|---|---|---|
|   | propylene dimer | propylene trimer | propylene tetramer | $C_6$ paraffins | $C_9$ paraffins | $C_{10}$ paraffins | phenol | hexyl-phenol | nonyl-phenol | dodecyl-phenol | alkyl-phenol | water |
| 1 | — | — | — | — | — | — | 99.9 | — | — | — | — | 0.1 |
| 2 | 5.1 | — | — | 0.2 | — | — | 35.3 | 56.7 | — | — | 2.5 | 0.3 |
| 3 | 0.2 | 7.1 | 0.3 | — | 3.5 | — | 41.4 | 0.1 | 46.2 | 0.2 | 0.7 | 0.7 |
| 4 | — | 0.2 | 12.4 | — | 0.4 | 6.8 | 38.9 | 0.3 | 0.7 | 39.6 | 0.5 | 0.4 |
| 5 | — | 5.1 | 7.8 | — | 0.1 | 0.1 | 79.4 | 0.1 | 2.8 | 2.6 | 0.1 | 1.9 |
| 6 | 11.0 | 8.7 | 0.2 | 8.4 | 0.1 | 0.1 | 41.2 | 11.8 | 7.2 | 0.2 | 4.8 | 0.1 |

TABLE 3

| Catalyst | Synthesis conditions of alkylphenols | | | Distillation conditions (separation of alkylphenols) | | Sulphur content in alkylphenol |
|---|---|---|---|---|---|---|
|   | alkylating agent (olefin) | phenol:olefin mole ratio | alkylation point | Pressure [mm Hg] | Temperature range [°C.] |   |
| Amberlyst-19 treated as described in Example 1 | propylene trimer | 3.0 | 100 | 5 | 145–150 | 7.4 |
| Amberlyst-19 treated as described in Example 2 | propylene trimer | 3.0 | 100 | 20 | 174–183 | 0.7 |
| Amberlyst-19 treated as described in Example 2 | propylene dimer | 1.5 | 80 | 175 | 115–117 | 0.5 |
| Amberlyst-19 treated as described in Example 3 | propylene tetramer | 2.0 | 100 | 2 | 150–160 | 0.4 |
| Wofatit FK4 treated as described in Example 4 | propylene trimer | 3.0 | 130 | 4 | 167–170 | 0.7 |
| Amberlyst-16 treated as described in Example 5 | propylene trimer | 2.0 | 90 | 2 | 136–140 | 0.8 |
| Amberlyst-16 treated as described in Example 5 | propylene tetramer | 2.0 | 90 | 30 | 200–230 | 0.5 |

TABLE 3-continued

| Catalyst | Synthesis conditions of alkylphenols | | | Distillation conditions (separation of alkylphenols) | | Sulphur content in alkylphenol |
|---|---|---|---|---|---|---|
| | alkylating agent (olefin) | phenol: olefin mole ratio | alkylation point | Pressure [mm Hg] | Temperature range [°C.] | |
| Amberlyst-16 treated as described in Example 5 | propylene tetramer | 3.0 | 120 | 3 | 150–168 | 0.6 |
| Amberlyst-15 treated as described in Example 6 | propylene trimer | 5.0 | 120 | 10 | 163–169 | 0.3 |
| Amberlyst-15 treated as described in Example 6 | propylene tetramer | 3.0 | 90 | 0.2 | 152–156 | 0.5 |
| Amberlyst XN1010 treated as described in Example 7 | propylene dimer | 2.0 | 60 | 55 | 52–57 | 0.9 |

We claim:

1. A method for reducing the water content of an ion exchange catalyst used in the synthesis of alkyl phenols, wherein the catalyst comprises a cation exchange bed of a sulphonated styrene-divinylbenzene copolymer containing 4–50% divinylbenzene, in hydrogen form, and having a moisture content of up to 70% by weight, comprising the steps or sequence of:

(1) passing phenol containing 0.01–1% by weight water through the cation exchange bed at a temperature in the range 50°– 100° C. to provide a resultant first effluent containing 50–99.5% by weight phenol and 0.5–50% by weight water, (2) running said resultant first effluent through a basic anion exchange resin to obtain a resultant second effluent, (3) removing water from the second effluent by distillation to obtain a dewatered phenol containing from 0.01–1% moisture by weight, (4) recycling said dewatered phenol through the cation exchange bed and its resultant first effluent throughout anion exchange resin until the water content of said cation exchanger is at or below 10%.

(5) washing the cation exchange bed at a temperature of 60 °–130° C. with a mixture consisting of 35–80% by weight phenol, 5–20 by weight $C_6$–$C_{12}$ olefins, 5–60% by weight Alkyl phenols having at least one substitute chain containing 6–12 carbon atoms, 0.1–5% by weight dialkyl phenols having substitute chains containing 6–12 carbon atoms, 0.1–15% by weight saturated $C_6$–$C_{12}$ hydrocarbons and 0.05–2% by weight water and collecting the effluent, (6) contacting the effluent with the basic ion exchange resin, (7) recycling said contacted effluent through said cation exchange bed and basic ion exchange resin until the cation exchange bed has a moisture contempt of not more than 3% by weight.

* * * * *